United States Patent [19]

Arntz et al.

[11] Patent Number: 4,539,409
[45] Date of Patent: Sep. 3, 1985

[54] PROCESS FOR PREPARING AROMATIC NITRILES

[75] Inventors: Dietrich Arntz; Günter Prescher, both of Hanau; Werner Burkhardt, Brachttal; Johannes Heilos, Seligenstadt; Reinhard Manner, Maintal, all of Fed. Rep. of Germany

[73] Assignee: Degussa Aktiengesellschaft, Frankfurt, Fed. Rep. of Germany

[21] Appl. No.: 542,965

[22] Filed: Oct. 18, 1983

Related U.S. Application Data

[62] Division of Ser. No. 390,446, Jun. 21, 1982.

[30] Foreign Application Priority Data

Jun. 26, 1981 [DE] Fed. Rep. of Germany ....... 3125062

[51] Int. Cl.$^3$ .................. C07D 213/57; C07C 120/14
[52] U.S. Cl. ................................. 546/286; 260/465 C
[58] Field of Search ............... 502/212, 309, 311, 312, 502/317, 318, 100, 10, 300; 427/213, 215; 260/465 C; 546/286

[56] References Cited

U.S. PATENT DOCUMENTS 3,637,797  1/1972  Decker et al. .................. 260/465 C
4,305,843  12/1981  Krabetz et al. ...................... 252/432

*Primary Examiner*—Dolph H. Torrence
*Attorney, Agent, or Firm*—Beveridge, DeGrandi & Weilacher

[57] ABSTRACT

A process is disclosed for preparing coated catalysts, inter alia, for gas phase oxidations in organic chemistry, comprised of an inert support and a coating of catalyst material enclosing this support, wherein a suspension of the starting material for the coating is sprayed onto an agitated bed of the support, while the suspending medium is being partially removed by a gas stream, and the raw material is then dried and heat-treated. For this purpose, the support bed is mechanically agitated and loosened by a gas stream blown in from below. The catalyst precursor containing a binder and, if appropriate, a pore-former is sprayed in an increasing amount from above onto the bed, the ratio between suspending medium sprayed on and drawn off remaining about constant. The thermal expansion coefficient of the precursor as a dry powder must not deviate by more than 15% from that of the support. The applied coating is densified by continuing the mechanical and fluidizing mixture motion, the material is then dried in a continuing gas stream and heat-treated, if appropriate after decomposition of an added pore-former.

2 Claims, No Drawings

PROCESS FOR PREPARING AROMATIC NITRILES

Div. of Ser. No. 3,940,446, 6-21-82.

The invention relates to a process for preparing abrasion-resistant coated catalysts formed of an inert support which has a rough surface and a particle size of 0.5 to 6 mm and a coating of active catalyst material enclosing the support and anchored in it, the process being carried out by agitating a bed of the support and spraying thereon a suspension of the starting material for the coating while partially removing the suspending medium by a gas stream of 20°-250° C., essentially constant residual moisture of the coating being maintained, and drying and heat-treating. The invention also relates to the catalysts produced thereby and uses of these catalysts in selected catalytic reactions.

It is known to use for catalytic oxidations catalysts in which the catalytically active constituents are arranged as a coating on an inert support which is in a particulate form or in some other shaped form.

This measure requires less of the expensive catalytically active catalyst material per reaction volume, and less expensive catalysts can thus be prepared.

In addition, the catalytic properties of catalysts can also be improved. Namely, this arrangement of active substance on the support surface; on the one hand, avoids local overheating phenomena, owing to the temperature-equalizing effect of the support mass, and, on the other hand, shortens the diffusion paths for gaseous reactants. Moreover, this arrangement makes it possible, by applying various layer thicknesses, purposely to produce more or less active catalysts (Austrian Pat. No. 226,672 corresponding to U.S. Pat. No. 3,232,977, the latter being relied on).

German Auslegeschrift No. 2,165,335 describes a process for preparing acrolein by oxidizing propylene with a gas containing molecular oxygen, in the gas phase at an elevated temperature in the presence of a catalyst, in which process a pulverulent composition containing, for example, the elements MoBiCoNiFeB-NaSnSiO adsorbed onto an inactive, porous support shape, such as $\alpha$-$Al_2O_3$. The material is here absorbed by applying the wet-milled catalyst composition onto porous $\alpha$-$Al_2O_3$ spheres of 5 mm diameter, followed by drying and heat-treatment.

German Offenlegungsschrfit No. 2,351,151 describes a process for preparing a coated catalyst intended for oxidation, ammoxidation or oxidative dehydrogenation of an olefin, in the preparation of which catalyst an inert support having a diameter of at least 20 $\mu$m is pre-wetted with a liquid and dry pulverulent catalyst material is then added and the mixture is slowly stirred.

According to German Offenlegungsschrift No. 2,250,200, a coated catalyst for cleaning exit gases from motor vehicles and industrial plants can be obtained by producing a catalytically active coating on shapes composed of heat-resistant support material by thoroughly mixing them, with the use of a liquid binder, with a pulverulent calcined active component which preferably has particle dimensions below 100 $\mu$m and then removing the binder by heating. Afterwards, the support core and the firmly adhering coating are present without significant mutual penetration.

Finally, the process described in European Laid-Open Application No. 0,015,569 involves, in the preparation of coated catalysts, applying an aqueous suspension of the catalytically active material onto agitated support particles, the suspension being sprayed at a certain constant rate onto the support, while the suspending medium is being partially removed by means of a gas stream of 20°-300° C., and an essentially constant residual moisture of the coating being maintained. U.S. Pat. No. 4,305,843 coresponds to the above European application and is relied on.

The catalysts which can be obtained by the known processes have the common disadvantage that in the case of thicker coatings, that is, coatings the amount by weight of which, relative to the catalyst, exceeds 20%, the abrasion resistance and impact strength of the coating are not fully satisfactory for use in large scale industrial fixed bed reactors.

In particular, a tendency for the coating to spall under the influence of temperature gradients was found in the case of coated catalysts manufactured by means of conventional coating pans or rotary disks, which only permit the passage of a drying gas stream across the agitated material.

Moreover, only a relatively wide particle size distribution, which is determined by the particular thickness of the coating of the individual particles of the catalyst, can be obtained by means of these devices.

However, a wide particle size distribution results in, on the one hand, a markedly higher pressure drop of catalyst beds and, on the other hand, the occurrence of strongly differing heats of reaction on the individual catalyst particles, which, in total leads to deterioration of selectivity.

The preparation process dealt with in European Laid-Open Application No. 0,015,569 requires the maintenance of a metering rate for suspension and drying gas which remains constant with time, in order to maintain the water content pension of the resulting coating during the spraying-on of the suspension at a virtually constant value. However, it is precisely this measure which, with increasing duration of the preparation operation, causes the outer surface of the coating to contain increasingly less liquid, which impairs or prevents the application of thicker coatings having sufficient mechanical strength.

Moreover, by guiding the dry gas stream over the surface of the support bed, a measure proposed there, only a moderate drying rate is obtained during the formation of the coating. The result of this is the unfavorable wide particle size distribution already mentioned.

The object of the invention is to provide a process for preparing coated catalysts which imparts to the latter abrasion resistance, temperature-change resistance and a narrow particle size distribution at the same time as good catalytic properties.

The invention relates to a process for preparing abrasion-resistant coated catalysts comprised of an inert support which has a rough surface and a particle size of 0.5 to 6 mm and a coating of active catalyst material enclosing this support and anchored in it, by agitating a bed of the support and spraying thereon a suspension of the starting material for the coating while partially removing the suspending medium by a gas stream at a temperature of 20°-250° C., essentially constant residual moisture of the coating being maintained, and drying and heat-treating, wherein a mixing motion is imparted to the support bed by mechanical action and the support bed is simultaneously loosened by blowing in from below a fluidizing, mixing-intensifying gas stream; a suspension of a precursor of the catalytically active material, which suspension contains a binder and, if appropriate, a pore-former, is passed countercurrent to the gas to this bed at a rate which increases with increasing thickness of the coating, the amounts of suspending medium drawn off and sprayed being maintained in a substantially constant ratio which is determined by the particular combination of support and precursor used and the thermal expansion coefficients of support and of dried pulverulent precursor being so chosen that they differ by at most 15%, and wherein after the spraying-on has been completed the coating is densified by continuing the increased mixing motion, the mechanical mixing motion is then stopped, the material is dried in a continuing gas stream and finally heat-treated, if appropriate after decomposition of an added pore-former.

The new coating process for support bodies proposes loosening up a support bed set in mixing motion by blowing in a gas stream from below, the gas stream passing through the fluidized charge effecting partial removal of the suspending medium. For carrying out this step, appropriately equipped mixing units are possible, such as, for example, special coating drums, coating pans or rotary disks. Those units are preferable in which drying air streams evenly through the entire bed.

The use of a so-called Driacoater in a countercurrent method, in which spray liquid and dry air flow in opposite directions has proved particularly advantageous. This piece of equipment has been described, inter alia, in German Offenlegungsschrift No. 2,805,801, relied on herein, and it primarily comprises a cylindrically or conically shaped and horizontally mounted drum. Dry air is introduced exclusively from below the underside of the bed of material via air ducts located in the outer jacket of the drum through hollow ribs arranged on the inside of the drum and which are perforated on the side facing away from the direction of rotation.

When the drum revolves, the bulge-shaped hollow ribs and the drying air blown in through them effect the fluidization and thorough circulation of the bed material; that the drying air flows evenly through the latter manifests itself in a uniformly and calmly downflowing intrinsic motion of the material. Moisture-rich exit air is drawn off above the bed via the hollow uptake mandrel in the axis of revolution of the drum.

For spraying the powder suspensions used in the process according to the invention, two-material nozzles are preferably used, by means of which, more simply than in the case of one-material nozzles, the desired feed rate, with any state of fine division, can be conveniently controlled.

The atomization is usually effected by means of compressed air of 0.5–2 bar, as a function of the necessary suspension throughput (which results from the size of charge, the desired thickness of the powder application and the time for preparation) by means of one or more nozzles of 2–4 mm diameter for pressures of the suspension in front of the nozzle of 1–3 bar.

For Driacoater units having charge capacities of 10–200 liter, it has proved advantageous to adjust the fluidizing gas stream to a specific flow rate of 15–50 $Nm^3$ per hour per liter of support and to heat it to 60°–100° C. Lower inlet air flow rates lead to markedly lower drying rates, less even flow through the entire bed due to wall effects along the drum walls and hence considerably longer preparation times. In contrast, air flow rates which are too high cause too severe drying the suspension on the way from the nozzle to the bed surface, which causes the resulting dried precursor powder to be carried with the exit air and inadequate moisture of the coating during application. It has been found that maintaining a constant moisture level of the resulting coating during the entire coating build-up is an essential prerequisite for obtaining a firmly adhering coating of active catalyst material firmly anchored in the support material. If the coating of the blanks during this coating build-up becomes too moist, several particles agglomerate with one another. However, if application is too dry the desired anchoring in the support and also strength of the coating cannot be obtained. It is also an essential insight that by maintaining a drying air which is constant in respect of temperature and rate the necessary constant moisture of the coating can be readily controlled by the amount of suspension sprayed on per unit time.

The fluidizing gas may be air, nitrogen, or other inert gases. Drying of the gas is not necessary, but if the gas is not dry, it should have nearly constant humidity.

To assign nominal values for such a control, the temperature above the bed or the moisture of the exit air can be used, both of which permit sensitive monitoring of the drying process. The most favorable nominal values themselves depend on the type of powder and on the temperature, the moisture and the amount of inlet air per unit volume of support material. Depending on the solids content of the suspension and the type of precursor, 10–50% of the sprayed-on suspending medium should remain in the coating during its build-up. It has been found that considerable improvement of the mechanical stability of the coating is obtained if not a constant nominal value but a decreasing temperature or an increasing exit air moisture are given. This makes possible, by corresponding program control, a fully automatic application of the precursor powder.

Water is preferably used as the suspending medium for the catalyst precursor present in powder form. Other liquids, such as, for example, alcohols, are not excluded and have in various points advantages over water: they may require less vaporization energy or permit better matching of the wetting and solubility behavior of the precursor of the catalytic material and the support substance. The latter can be influenced in the case of aqueous suspensions only by adding binders. However, the advantage of organic solvents is contrasted with the disadvantage of forming ignitable mixtures with the drying air and requiring special exit air cleaning units. The suspending medium should be inert; that is, non-reactive during the course of the preparation.

The solids content of the suspension is best so adjusted that the suspension is comprised of 20–80, preferably 40 -70, % by weight, in particular 55% by weight, of pulverulent precursor.

Solids contents which are too high can cause blockages in the feed and spray system for the suspension. Solids contents which are too low, however, require unnecessarily prolonged preparatin times. The empirically determinable solids content which is most favorable in a particular case depends on the properties of the precursor used and its interaction with the suspending medium and, in the case of the catalysts prepared within the scope of the examples, is 55% for the propene oxidation.

It has also been found that it is possible to obtain a marked improvement in the abrasion resistance of supported catalysts by the use of binders as known from granulation. Their content in the suspension depends on the type of binder and is as a rule between 0.5 and 10%. While the lower limit is fluid and the minimum amount necessary to ensure improvement of the abrasion resistance, in the case of binder concentrations which are too high the drying rate during the preparation of the coating is frequently reduced. For the precursors of the active catalyst component which were used, the best results were obtained with 2-5%, in particular about 4%, by weight of glucose or urea.

Other binders include starch, sugar, sorbite, gum arabicum, propylene glycol, stearic acid, oleic acid and glycerol. The function of the binder is to tackify the surface of the carrier and the surface of the precursor.

In certain reactions, such as, for example, the oxidation of propene to acrolein, a retardation of the reaction due to pore diffusion is observed in particular when using coated catalysts having a high proportion of active phase, that is thick coatings. It has now been found that the addition of finely divided pore-formers sparingly soluble in the suspending medium such as pentaerythritol, polymethyl methacrylate, polystyrene, polyvinyl alcohols or the like, can reduce this retarding influence on the reaction by the formation of macropores.

The pore-former enhances transport of reacting molecules within the catalyst system. It may be a polymer or a monomer and should be only slightly soluble in the suspending medium. The pore-former must be capable of being burned off during the tempering step.

The preferable content in the suspension of pore-former is 1-10% by weight. It is a prerequisite for the action of the pore-former that it can be removed again below the heat-treatment by thermolysis or oxidation of the built-up coating.

The invention explicitly proposes using, for the build-up of the coating, a precursor of the catalytically active material. The term "precursor" is to be understood as meaning that the precursor material already contains all the ingredients required for producing the complete catalytically active material by a subsequent specific heat treatment.

The precursor is a preformed catalytic material in powder which may be a dried coprecipitate or a coprecipitate which has been heat-treated below the temperature of the final tempering step. As shown in the examples, the precursor may be oxidic or hydroxidic and is made from salt solutions.

In the process according to the invention, preferably a coprecipitate from combined salt solutions of catalytically active elements, which coprecipitate is dried or has been calcined below the heat-treatment temperature, is used as the precursor of the catalytically active material.

The composition of this coprecipitate and its particular preparation is not specific to the process according to the invention, but depends on the desired catalytic action in the reaction where the coated catalyst is used. Usually, the precursor can be prepared analogously to known unsupported catalysts. To obtain good suspendability of the precursor in the suspending medium and a trouble-free feed of the suspension, a particle size distribution of 1-150 μm, having a maximum preferably within the range of 1.5-30 μm has proved advantageous.

The process according to the invention makes possible the preparation of coated catalysts in which the amount of the pulverulent precursor is 0.1-2 times the weight of the support, this range not resulting from specific limits of the preparation process but rather from practical considerations concerning the use of the catalysts according to the invention. This means that in principle even those compositions can be prepared by the process according to the invention which are outside the range indicated.

The invention also explicitly proposes that the thermal expansion coefficients of support and precursor are to be so adjusted that they substantially agree and differ at most by not more than 15%. For if these coefficients differ by more, the coating will crack in the subsequent heat treatment step.

These cracks can become so large that flaky spalling of the coating takes place. In any case, the occurrence of cracks is associated with a sharp reduction of the mechanical stability of the coating, that is the abrasion resistance. It has been found that matching of the thermal expansion coefficients by selecting a suitable support is only possible in some cases and is seldom adequate, since possible inert supports are all within the relatively narrow range from $50-90\times10^{-7}/°C$. (for one-dimensional expansion).

It has now been found, surprisingly, that the thermal expansion coefficient of the precursor powder can be matched to the coefficient of the support by a heat pretreatment at 250°-600° C. The particular precise conditions depend on the composition of the precursor and on the support to be used. Care must be taken here that this matching is to be carried out not for a certain temperature but for the entire temperature range of the subsequent heat treatment (the tensions between coating and support which occur in this heat treatment are responsible for possible crack formation). This means that an exact matching, which would presuppose a firmly defined reference temperature, is not possible. This is particularly due to the fact that, in the materials to be used according to the invention, different temperature dependencies of the expansion coefficients are usually given for precursor and support.

Within the scope of the invention, the preparation of improved coated catalysts for four important gas reactions of organic chemistry which use heterogeneous catalysis is to be particularly emphasized, since it is precisely these processes which can be considerably improved by means of these catalysts.

These reactions are the catalytic oxidation of propylene or isobutene to acrolein or methacrolein respectively, the catalytic gas phase oxidation of acrolein and methacrolein to acrylic acid and methacrylic acid respectively, the catalytic gas phase oxidation of methanol to formaldehyde and the ammoxidation of aliphatic and aromatic hydrocarbons to nitriles. For each of these reactions, the preparation of a suitable coated catalyst using a precursor material which is already known in itself and which is only in need of the final heat treatment determining the catalytic properties will be indicated below.

According to a preferable embodiment of the invention, the precursor for a coated catalyst for preparing acrolein or methacrolein from propylene or isobutene accordingly used is an oxidic powder of the composition:

$$Ni_aCo_bFe_cBi_dP_eMo_fO_x$$

in which a is a number from 2-20, b is a number from 0-15, a and b are a number from 2-20, c is a number from 0.1-7, d is a number from 0.1-4, e is a number from 0.1-4, f is about 12 and x is a number from 35-85, and 0.2 to 5% of tantalum or samarium, calculated as $Ta_2O_5$ or $Sm_2O_3$, and, if appropriate, also 0.05 to 3.0% of an alkali metal or alkaline earth metal, calculated as oxide, if appropriate on a support substance composed of a layer lattice silicate and/or highly dispersed silica—in the first case (that is, when the silicate plus silica are used) in a weight ratio of 10:1 to 1:1—are additionally used, and the coated catalyst is heat-treated for 0.05-5 hours at 520°-650° C. When an alkali metal or alkaline earth metal is used, the elements K, Na and Mg are preferable. Modification of these catalyts by alkali metals and alkaline earth metals is known in the art.

Layer lattice silicate is a silicate with a leaf structure and is easily cleaved along the crystal lattice network. Examples of such substances are montmorillonite, talc, and kaolinite. High dispersion silicas are made by flame hydrolysis of halosilanes, such as $SiCl_4$. These are sometimes called pyrogenic silica. Examples are Aerosil and Cab-O-Sil.

According to a further preferable embodiment of the invention, the precursor used for a coated catalyst for preparing acrylic acid and methacrylic acid from acrolein and methacrolein respectively is an oxidic powder of the composition:

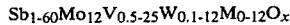

in which M denotes at least one of the elements lead, silver, copper, tin, titanium or bismuth and the coated catalyst is heat-treated for 0.05-5 hours at 320°-450° C.

Moreover, it is possible for the precursor used for a coated catalyst for the oxidation of methanol to formaldehyde advantageously to be an oxidic powder composed of molybdenum and iron in an $MoO_3:Fe_2O_3$ ratio of 10 and which may have admixed 3-60% by weight of $TiO_2$ and the coated catalyst to be heat-treated for 3-10 hours at 300°-500° C.

Finally, the precursor used for a coated catalyst for the ammoxidation of alkyl-substituted aromatic and heteroaromatic hydrocarbons can be an oxidic powder composed of the oxides of antimony and vanadium in a ratio of 1.1:1 to 50:1 and which additionally contains at least one of the elements iron, copper, titanium, cobalt, manganese and nickel and, if appropriate, support substance composed of layer lattice silicate and highly dispersed silica, and the resulting coated catalyst is heat-treated for 2-8 hours between 600° and 1,100° C.

Suitable support materials for the coated catalysts obtainable according to the invention and which can be advantageously used in these and also in other reactions have proved to be, in particular, α-alumina, aluminum silicate, magnesium silicate or silicon carbide. These are inert under the conditions of the reaction described herein. As regards the shape of the support, the process has no special demands, but spherical supports are preferable.

Nonporous or slightly porous magnesium silicate or silicon carbide is used above all when it is intended to apply the active phase only to the surface of the support and not to introduce the phase into the cavities of the support. In contrast, the catalytic material is more strongly protected and better anchored in the cavities of macroporous α-aluminas and alumosilicates and, in coatings which are not too thick (less than 20% by weight of active phase), requires a coating which is not so hard. The macropores of aluminum silicates and α-alumina should be within the range of 2-2,000, preferably 20-300, μm (90% value), in order, on the one hand, to ensure adequate strength of the support but, on the other hand, to permit the depositing of active phase in the pores.

From the point of view of a favorable behavior during coating build-up slightly porous or nonporous supports have advanatges, since, in the case of these materials, a lower liquid loading of the support takes place at the start of the preparation and the moisture leaving the pores at the end of the preparation in the drying process is more difficult to control in the case of macroporous supports.

The invention also proposes that the support material should have a rough external surface because this increases the bond strength of the coating by in-depth anchoring of the catalytically active material in the support and permits uniform application to the entire support surface. In the case of smooth support material surfaces, a flaky, irregular, thick application is usually observed. It has been found to be particularly advantageous if the support surface has a roughness, characterized by the middle roughness value according to DIN 4,768/1, measured by means of the Hommel roughness meter of 5-50 μm.

The invention, in addition to describing the improved preparation processes for coated catalysts, also relates to the four uses of these coated catalysts already mentioned and to the catalysts per se.

The invention is illustrated in more detail below by means of illustrative embodiments:

EXAMPLE 1

The coprecipitate for the preparation of the active catalyst phase was prepared in a manner known from German Pat. No. 2,049,583, relied on herein, by successively adding with stirring a solution of 0.3 kg of samarium oxide $Sm_2O_3$ in 3.5 kg of 38% strength nitric acid, 5.8 kg of pyrogenic silica, Aerosil ®, 10.8 kg of montmorillonite, a solution of 23.4 kg of ammonium molybdate $(NH_4)_6Mo_7O_{24}.4H_2O$ in 31.4 kg of 3.5% strength phodphoric acid and a solution of 5.4 kg of bismuth nitrate $Bi(NO_3)_3.5H_2O$ in 4.5 kg of 7.7% strength nitric acid to a solution of 32.3 kg of nickel nitrate $Ni(NO_3)_2.6H_2O$, 1 kg of cobalt nitrate $Co(NO_3)_2.6H_2O$ and 4.5 kg of ferric nitrate $Fe(NO_3)_3.9H_2O$ in 38 kg of water. The resulting suspension of the coprecipitate was dried on a drum dryer, calcined at 530° C. in a revolving tube and then milled. The resulting powder of the precursor of the catalytically active material had a particle ize distribution of 2-40 μm (>90%, maximum amount 15 μm) and, at 400° C., a thermal expansion coefficient of $81 \times 10^{-7}$/°C.

By suspending 6.5 kg of this precursor powder in 4.7 kg of water with the addition of 0.5 kg of D-glucose as binder and 0.3 kg of pentaerythritol (type R, made by Degussa) as pore-former, the suspension for the starting material of the coating was prepared. The supports chosen for this precursor material were fired steatite spheres which have a diameter of 4 mm, are virtually nonporous and have a rough surface (middle roughness value 25 μm according to DIN 4,768/1) and the longitudinal thermal expansion coefficient which is $90 \times 10^{-7}$/°C.

6 kg of this support were introduced into a Driacoater 500 and given a vigorous mixing and flowing motion in this unit by blowing in 2 m³/minute of preheated air at 80° C. and revolving the drum at 20 rpm.

Then 0.4 liter of the suspension was sprayed in 2 minutes by means of a two-material nozzle onto the support thus agitated. The spraying-on of the remaining suspension was controlled via the exit air temperature from the pan in such a manner that all the time a constant moisture of the coating was observed. In this stage, the exit air temperature fell from initially 48° C. to 39° C. at the end of the application of the suspension (after 60 minutes), and the rate at which the suspension was applied increased from 0.096 to 0.104 liter per minute.

At the end of the spraying-on process, there followed, while the drum continued to revolve, a densification phase of 5 minutes and then a 20 minute drying phase at a single pan revolution per minute.

After air drying overnight, the pore-former was decomposed in the revolving tube at 400° C. and a mean residence time of 15 minutes. The catalyst was activated at 550° and 15 minutes residence time, likewise in the revolving tube.

The coated catalyst obtained had a hard, crack-free coating. The mean diameter of the coated catalyst obtained was 5.25 mm with a standard deviation of 0.3 mm. Abrasion was determined as amount of abraded material smaller than 2 mm after 7 minutes in a La-Roche Friabilator by rolling and falling wear at 20 rpm and it was less than 0.2% by weight for the heat-treated coated catalyst. After a heat treatment of 100 cycles of heating-up and cooling-down, in which the catalyst was heated, in each case in 0.5 hour, from 250° C. to 400° C. and then cooled down again to 250° C., the value had not significantly increased and was 0.2% by weight.

In a falling test, free fall of 100 ml of catalyst onto a hard surface through a 3.4 m long tube having an internal diameter of 20 mm, the proportion of broken material of <2 mm produced was 0.03% by weight.

COMPARATIVE EXAMPLE 1

The precursor powder was prepared as in Example 1, only with the difference that the drum-dried coprecipitate was calcined at 410° C. in the revolving tube. The thermal expansion coefficient of the powder was then $50 \times 10^{-7}/°C.$ at 400° C.

A coated catalyst was prepared analogously to Example 1 by means of this precursor powder. In the two revolving tube processes, the decomposition of pore-former and the heat treatment, strong abrasion took place (about 5% by weight). The coating was severely cracked and, in places, pieces had spalled off. For this catalyst, for which the thermal expansion coefficient of the precursor of the support by a suitable heat treatment, abrasion in a La-Roche Friabilator was 15% by weight.

COMPARATIVE EXAMPLE 2

The precursor powder prepared according to Example 1 was used for preparing a catalyst in a coating pan. For this purpose, 30 kg of the steatite support used in Example 1 were initially introduced into the 50 kg coating pan and given a mixing motion by a rotation of the pan at 21 rpm at a pan inclination of 20°. Then 31 kg of the precursor powder were suspended together with 2.5 kg of D-glucose and 1.5 kg of pentaerythritol in 22 liters of water. The surface of the agitated bed was impinged with heated air at 90° C. with a rate of 200 m³ per hour. To apply the coating, the suspension was sprayed on through a two-material nozzle at a flow rate falling gently from initially 0.5 liter of suspension per minute to 0.48 liter per minute after one hour. When application was complete (about 80 minutes), the coating was densified for a further 10 minutes in the pan which continued to run. The resulting coated catalyst was dried for 15 hours at 40° C., the pore-former was decomposed at 400° C. in the revolving tube, and a heat treatment was carried out in the revolving tube at 550° C. and 15 minutes residence time.

The resulting catalyst had the following physical properties, the mean diameter was 5.3 mm with a standard deviation of 0.68 mm.

The rolling and falling wear in a La-Roche Friabilator (20 rpm, 7 minutes running time) was 1% by weight before and 1.2% by weight after a temperature change stress treatment between 250° and 400° C. (100 cycles in 50 hours). In a falling test of 100 ml of catalyst through a 3.4 m long tube having an internal diameter of 20 mm, the proportion of broken material of <2 mm produced was 0.2% by weight.

EXAMPLE 2

The catalytic effect of the catalyst prepared in Example 1 was tested in an industrial reactor tube having an internal diameter of 20.5 mm and being externally cooled by a salt bath, with a catalyst bed depth of 2.7 m by means of the conversion of propene to acrolein.

(a) Feeds of 5 moles of propene per hour, 40 moles of air per hour and 10.1 moles of $H_2O$ per hour produced, at a salt bath temperature of 351° C., a conversion of 94%, an acrolein starting yield of 79.2 and a total selectivity for acrolein and acrylic acid of 92.5%.

(b) Feeds of 5 moles of propene per hour, 38 moles of air per hour and 29 moles of recycled exit gas per hour (composition: 7% of $O_2$, 1% of propene and 92% of inert gas; e.g. propane, nitrogen, carbon dioxide and water) produced, at a salt bath temperature of 355° C., a conversion of 94.9%, an acrolein yield of 79.5% and a selectivity for acrolein and acrylic acid of 92%.

EXAMPLE 3

A raw catalyst powder corresponding to German Pat. No. 2,145,851 was used as precursor of the catalytically active material. This powder was subjected for 8 hours at 300° C. to a heat treatment. It had a composition of 67.1% by weight of $MoO_3$, 12.8% weight of $Fe_2O_3$ and 20.1% by weight of $TiO_2$. The main range (90%) of the particle size distribution was between 1 and 10 μm, with the 50% value at 1.7 μm. The thermal conductivity of the catalytic material was $73 \times 10^{-7}/°C.$ 2 kg of this powder were suspended in 2 kg of water after the addition of 0.12 kg of urea (as binder). 6 kg of aluminum silicate supports having a specific surface area of less than 1 m²/g, a macroporosity where 90% of the pores were between 30 and 250 μm, a surface roughness according to DIN 4,768/1 with a middle roughness value of 40 μm, a diameter of 48 mm and a thermal expansion coefficient of $69 \times 10^{-7}/°C.$ (at 400° C.) were introduced into a Driacoater 500 as supports for this precursor material. The support was given a thorough mixing and flowing motion by blowing in preheated air at 95° C. at a rate of 4 m³ per minute and revolving the drum at 20 rpm.

The suspension of the precursor was sprayed in the course of 75 minutes onto the fluidized support in such a way that the exit air temperature sank from initially 50° to 44° C. at the end of the application stage. After a further densification phase of 5 minutes in the Driacoater while further fluidizing and drying the raw coated catalyst, the latter was air-dried for about 15 hours and then heat-treated for 5 hours at 425° C. in an air stream. The abrasion resistance in the La-Roche Friabilator standard test (7 minutes, 20 rpm) was 0.3% by weight.

5,180 g (about 3,760 ml) of the finished coated catalyst were evenly packed into nine tubes (internal diameter 18.1 mm) of a tube bundle reactor. The bed depth of catalyst was about 173 cm in the tubes, some of which were equipped with laterally introduced temperature sensors.

The tube bundle reactor was cooled by a circulated stream of molten salt. The salt bath temperature was 301° C. A preheated gas stream at about 290°–300° C. was fed at a rate of 4,640 liters (S.T.P.) per hour into the reactor and had the following composition: 11.1% by volume of methanol and 12.8% by volume of oxygen with the rest being inert gases, mainly nitrogen in addition to small amounts of steam (about 0.5% by volume). The maximum temperature in the catalyst bed was 355° C. The gas leaving the reactor was immediately cooled down; the condensable products were then absorbed into water. A yield of 93.1% of formaldehyde, relative to the amount of methanol used, was obtained at a conversion of 99% of the methanol used over an accounting interval of 72 hours.

EXAMPLE 4

A precursor powder corresponding to Example 1 of German Pat. No. 2,009,172, relied on herein, and containing antimony, molybdenum, vanadium and tungsten in a molar ratio of 6:12:3:1.2 was prepared. The drum-dried coprecipitate was largely converted into the oxides by calcination at 250° C. in a revolving tube and then milled. The powder then had a particle size distribution with a main range (>90%) of 2–50 μm with a maximum at 4.7 μm and a thermal expansion coefficient at 400° C. of $86 \times 10^{-7}/°C$.

6 5 kg of this precursor powder were suspended in 3.5 kg of water together with 0.2 kg of glucose as binder and this suspension was sprayed on in the course of 75 minutes onto 6 kg of steatite support (as in Example 1) in a Driacoater.

During this step, the support was given a thorough flowing and mixing motion by preheated air at 80° C. and rotation of the pan. The activating, final heat treatment took place at 360° C. in a revolving tube with a residence time at 15 minutes. The abrasion resistance in the La-Roche Friabilator standard test (7 minutes, 20 rpm) was 0.05% by weight.

58 g of this coated catalyst were packed into a reactor having an internal diameter of 16 mm and being externally by a salt melt. A gas stream comprising 1.4 moles of air hour, 0.5 mole of water per hour and 0.16 mole of acrolein hour was passed over the catalyst at a salt bath temperature of 301° C., and a conversion of 98.8% and an acrylic acid yield of 94.5%, relative to acrolein used, were obtained.

EXAMPLE 5

A precursor powder was prepared in accordance with German Pat. No. 2,009,172 by coprecipitation of 23.3 kg of antimony trioxide, 4.7 kg of ammonium metavanadate, 12.8 kg of titanium dioxide, 11.7 kg of montmorillonite and 5.8 kg of pyrogenic silica, drum drying and 0.3 hour's heat treatment at 450° C. The resulting powder, after milling, had a particle size spectrum of 1–20 μm (90%) with a maximum of 15 μm and a thermal expansion coefficient at 400° C. of $65 \times 10^{-7}/°C$.

9 kg of this precursor powder were suspended in 6 kg of water together with 0.4 kg of glucose as binder and 0.6 kg of pentaerythritol, and sprayed, in a Driacoater, in 85 minutes onto 6 kg of aluminum silicate spheres (as Example 3). In this step, the support was fluidized by preheated air at 80° C. and revolving the pan, and the spraying process was controlled in such a way that the exit temperature from the pan was lowered from initially 47° C. to 37° C. at the end.

After air drying (15 hours), the coated catalyst was finally heat-treated by being successively treated in a muffle furnace for 3 hours at 550° C., 1 hour at 650° C. and 3 hours at 770° C. The abrasion of the finished coated catalyst, in the La-Roche Friabilator standard test, was 0.1% by weight.

The catalyst was excellently suitable for the ammoxidation of aromatic and heteroaromatic hydrocarbons.

EXAMPLE 6

2 kg of the precursor powder prepared as in Example 1 were suspended in 1.9 kg of water with the addition of 0.05 kg of glucose as binder. In a Driacoater 500, 6 kg of an aluminum silicate support having a specific surface area of less than 1 m²/g, a diameter of 4.8 mm, a macroporosity where 90% of the pores were between 70 and 500 μm, a surface roughness according to DIN 4,768/1 with a middle roughness value of 48 μm and a thermal expansion coefficient at 400° C. of $72 \times 10^{-7}/°C$. were given a thorough mixing and flowing motion by blowing in preheated air at 70° C. at a rate of 2 m³/min and by turning the drum at 12 rpm, and the suspension analogous to Example 1 was sprayed in the course of 35 minutes onto the support thus agitated in such a way that the exit air temperature sank from initially 43° C. to 38° C. After drying, the raw catalyst was activated at 575° C. in a revolving tube. The abrasion, measured in a La-Roche Friabilator, was 0.2% by weight.

EXAMPLE 7

A precursor powder was prepared according to Example 1, only with the difference that 0.4 kg of potassium nitrate was additionally added to the samarium oxide solution. The precursor powder calcined at 470° C. in a revolving tube had a thermal expansion coefficient of $80 \times 10^{-7}/°C$.

9 kg of this precursor material were suspended in 5.3 kg of water together with 0.7 kg of pentaerythritol (pore former) and 0.8 kg of glucose (binder) and the suspension was sprayed in a Driacoater onto 6 kg of thoroughly agitated steatite supports (as in Example 1). In this step, the inlet air supplied at 2.5 m3 per minute was preheated to 85° C. and the suspension sprayed on in the course of 95 minutes was metered at such a rate that the exit air temperature sank from 51° C. initially down to 42° C. After drying, decomposition of pore-former and binder at 400° C. and activation at 550° C. in a revolving tube, the catalyst had an abrasion of 0.3% by weight in a La-Roche Friabilator.

EXAMPLE 8

A precursor powder was prepared analogously to Example 1 by successively adding with stirring a solution of 18.4 kg of ammonium molybdate $(NH_4)_6Mo_7O_{24}.4H_2O$ in 24.1 kg of 3.1% strength phosphoric acid, a solution of 7 kg of bismuth nitrate $Bi(NO_3)_3.5H_2O$ in 7.0 kg of 0.8% strength nitric acid and 6 kg of pyrogenic silica (Aerosil ®200) to a solution of 6.7 kg of nickel nitrate $Ni(NO_3)_2.6H_2O$, 12.3 kg of cobalt nitrate $Co(NO_3)_2.6H_2O$ and 6.9 kg of ferric nitrate $Fe(NO_3)_3.9H_2O$ in 30.4 kg of water. The resulting coprecipitate was dried at 140° C. on a drum dryer and calcined at 535° C. in a revolving tube and then milled in a pin mill.

The resulting powder had a particle size distribution of 5–80 μm (90% value) with a maximum at 30 μm and a thermal expansion coefficient of $85 \times 10^{-7}$/°C.

An abrasion-resistant catalyst was prepared in a Driacoater 500 in a manner corresponding to Example 1 from 7.5 kg of this precursor powder with an addition of 0.6 kg of glucose and 0.5 kg of pentaerythritol in 6.2 kg of water and 6 kg of steatite support. The abrasion was 0.25% by weight in a La-Roche Friabilator.

EXAMPLE 9

A precursor powder was prepared as in Example 8, but with the addition of 0.2 kg of $KNO_3$ to the first solution. The resulting powder had a particle size distribution of 3–70 μm (90% value) with a maximum at 25 μm and a thermal expansion coefficient of $84 \times 10^{-7}$/°C.

An abrasion-resistant coated catalyst was prepared in a Driacoater 500 in a manner corresponding to Example 1 from 5.5 kg of this precursor powder with 0.4 kg of glucose in 4.5 kg of water and 6 kg of steatite support. The abrasion was 0.3% by weight in a La-Roche Friabilator.

EXAMPLE 10

50 ml of the catalyst prepared in Example 8 were packed into a tube reactor which had an internal diameter of 16 mm and was externally temperature-controlled to 362° C. by a salt bath. Feeds, per hour, of 0.25 mole of propene, 45 liters (S.T.P.) of air and 9.5 g of water produced a conversion of 92.5%, an acrolein yield, relation to propene used, of 80.5% and a total selectively, relative to propene used, of 95.8%.

EXAMPLE 11

50 ml of the catalyst prepared in Example 6 were packed into a reactor which had an internal diameter of 16 mm and was externally temperature-controlled to 370° C. by a salt bath. Feeds, per hour, of 0.15 mole of isobutene, 35 liters (S.T.P.) of air and 10.5 g of water produced a conversion of 91%, a methacrolein yield of 74.1%, relative to isobutene fed in, and a total yield of methacrolein and methacrylic acid of 82.4%.

EXAMPLE 12

50 ml of the catalyst prepared in Example 7 were packed into a reactor which had an internal diameter of 16 mm and was externally temperature-controlled to 355° C. by a salt bath. Feeds, per hour, of 0.15 mole of t-butanol, 35 liters (S.T.P.) of air and 10.5 g of water produced a conversion of 92.8%, a methacrolein yield of 75.2%, relative to t-butanol fed in, and a total yield of methacrolein and methacrylic acid of 81.9%.

EXAMPLE 13

50 ml of the catalyst prepared in Example 9 were tested as in Example 11 at a salt bath temperature of 382° C. The conversion was 93.6%, the methacrolein yield was 75.6%, relative to isobutene fed in, and the total selectivity for methacrolein and methacrylic acid was 82.9%.

EXAMPLE 14

80 ml of the catalyst prepared according to Example 5 were packed into a reactor which had an internal diameter of 20.5 mm and was externally temperature-controlled to 430° C. Feeds, per hour, of 0.12 mole of β-picoline, 80.5 liters (S.T.P.) of air, 16 liters (S.T.P.) of ammonia and 19 g of water produced a conversion of 89.5% and a selectivity for nicotinoyl nitrile of 79% relative to β-picoline used.

We claim:

1. In a process for preparing aromatic and heteroaromatic nitriles by ammoxidation of alkyl-substituted aromatic and heteroaromatic hydrocarbons, the improvement which comprises using as the catalyst an abrasion-resistant coated catalyst formed of an inert support which has a rough surface and a particle size of 0.5 to 6 mm and a coating of active catalyst material enclosing this support and anchored in it, said catalyst having been prepared by a process comprising agitating a bed of the inert support and spraying thereon a suspension of a precursor for said active catalyst material in a suspending medium while partially removing the suspending medium by a gas stream at a temperature of 20°–250° C., essentially constant residual moisture of the coating being maintained, drying and heat-treating wherein a mixing motion is imparted to the support bed by mechanical action and the support bed is simultaneously loosened by blowing in from below a fluidizing, mixing-intensifying gas stream; said precursor being an oxidic powder composed of the oxides of antimony and vanadium in a ratio of 1.1:1 to 50:1 and which additionally contains at least one of the elements iron, copper, titanium, cobalt, manganese and nickel, which suspension contains a binder, and which suspension is passed countercurrent to the gas in this bed at a rate which increases with increasing thickness of the coating, the amounts of suspending medium drawn off and sprayed being maintained in a substantially constant ratio which is determined by the particular combination of support and precursor used, the thermal expansion coefficients of support and of dried pulverulent oxidic precursor being so chosen that they differ by at most 15%, and wherein after the spraying-on has been completed the coating is densified by continuing the increased mixing motion, the mechanical mixing motion is then stopped, the material is dried in a continuing gas stream and finally heat treated for 2–8 hours between 600° and 1100° C.

2. The process of claim 1, wherein a layer lattice silica and a high dispersed silica are further added to said oxidic powdered precursor admixture.

* * * * *